(12) United States Patent
Kang et al.

(10) Patent No.: US 7,285,514 B2
(45) Date of Patent: Oct. 23, 2007

(54) METHOD FOR PREPARING CATALYST FOR PARTIAL OXIDATION OF ACROLEIN

(75) Inventors: Jung-Hwa Kang, Seoul (KR); Won-Ho Lee, Daejeon (KR); Min-Ho Kil, Busan (KR); Hyun-Jong Shin, Naju (KR); Byung-Yul Choi, Seoul (KR); Yeon-Shick Yoo, Naju (KR); Young-Hyun Choe, Jeollanam-do (KR); Ju-Yeon Park, Naju (KR)

(73) Assignee: LG Chem, Ltd., Seoul (KR)

( * ) Notice: Subject to any disclaimer, the term of this patent is extended or adjusted under 35 U.S.C. 154(b) by 331 days.

(21) Appl. No.: 10/691,665

(22) Filed: Oct. 24, 2003

(65) Prior Publication Data

US 2004/0116283 A1 Jun. 17, 2004

(30) Foreign Application Priority Data

Nov. 29, 2002 (KR) ................. 10-2002-0075283

(51) Int. Cl.
 B01J 23/00 (2006.01)
 B01J 23/22 (2006.01)
 B01J 20/00 (2006.01)
 B01J 21/00 (2006.01)

(52) U.S. Cl. .............. 502/306; 502/310; 502/311; 502/312; 502/313; 502/314; 502/316; 502/317; 502/318; 502/319; 502/320; 502/321; 502/322; 502/323; 502/248; 502/255; 502/355; 502/415; 502/439

(58) Field of Classification Search ........... 502/306, 502/310–314, 316–318, 319–323, 355, 415, 502/439, 248, 255
See application file for complete search history.

(56) References Cited

U.S. PATENT DOCUMENTS

| | | | |
|---|---|---|---|
| 3,898,267 A * | 8/1975 | Caporali et al. ......... 558/322 |
| 4,113,769 A * | 9/1978 | Padovan et al. ......... 562/534 |
| 4,166,190 A * | 8/1979 | White et al. ............ 562/534 |
| 4,259,211 A * | 3/1981 | Krabetz et al. .......... 502/178 |
| 4,271,040 A * | 6/1981 | Khoobiar ............... 502/211 |
| 4,318,738 A * | 3/1982 | Masumoto et al. ....... 148/304 |
| 4,321,160 A * | 3/1982 | Farrington et al. ....... 502/209 |
| 4,471,061 A * | 9/1984 | Shaw et al. ............. 502/34 |
| 4,539,232 A | 9/1985 | Burzynski et al. |
| 4,547,588 A * | 10/1985 | Khoobiar ............... 562/535 |
| 5,086,145 A | 2/1992 | Morimoto et al. |
| 6,171,571 B1 * | 1/2001 | Bedard et al. .......... 423/594.7 |
| 6,525,217 B1 * | 2/2003 | Unverricht et al. ...... 562/544 |
| 6,740,779 B1 * | 5/2004 | Tenten et al. .......... 562/598 |
| 6,881,702 B2 * | 4/2005 | Arnold et al. .......... 502/311 |
| 6,914,029 B2 * | 7/2005 | Davis et al. ........... 502/150 |

FOREIGN PATENT DOCUMENTS

WO WO/97/22652 A1 6/1997

OTHER PUBLICATIONS

Claims from TW100305 (Jan. 1, 1999).
Claims from TW238321 (Jan. 11, 1995).

* cited by examiner

*Primary Examiner*—Cam N. Nguyen
(74) *Attorney, Agent, or Firm*—Birch, Stewart, Kolasch & Birch, LLP

(57) ABSTRACT

The present invention relates to a method for preparing a catalyst for partial oxidation of acrolein, particularly to a method for preparing a catalyst for partial oxidation of acrolein that has a superior acrolein conversion rate, acrylic acid activity, selectivity, and yield, by introducing a base solution and an acid solution into a catalyst suspension prepared by dissolving salts of metal ingredients of the catalyst in water to control the acidity of the catalyst suspension, contacting the catalyst suspension of which acidity is controlled with an inert support to support the catalyst thereon, and then drying and firing the supported catalyst.

9 Claims, No Drawings

METHOD FOR PREPARING CATALYST FOR PARTIAL OXIDATION OF ACROLEIN

This Nonprovisional application claims priority under 35 U.S.C. § 119(a) on Patent Application No(s). 2002-0075283 filed in Korea on Nov. 29, 2002, the entire contents of which are hereby incorporated by reference.

BACKGROUND OF THE INVENTION (a) Field of the Invention

The present invention relates to a method for preparing a catalyst for partial oxidation of acrolein, and more particularly to a method for preparing a catalyst for partial oxidation of acrolein that has a superior acrolein conversion rate and that can improve acrylic acid activity, selectivity, and yield.

(b) Description of the Related Art

Up to now, various methods for effectively preparing an acrylic acid by gas phase contact oxidation have been suggested. For example, Japanese Laid-open patent publication No. 44-12129 discloses a catalyst comprising molybdenum, vanadium, and tungsten; Japanese Laid-open patent publication No. 49-11371 discloses a catalyst comprising molybdenum, vanadium, copper, tungsten, and chrome; Japanese Laid-open patent publication No. 50-25914 discloses a catalyst comprising molybdenum and vanadium; and Japanese Laid-open patent publication No. 52-85091 discloses a catalyst comprising one or more ingredient selected from the group consisting of molybdenum, vanadium, antimony, copper, and germanium.

In addition, EP 023,859 describes that acrolein conversion rate and acrylic acid yield are varied according to a catalyst-forming method when catalyst ingredients and their ratio are identical, and discloses a method for preparing a catalyst having a high acrylic acid yield. Additionally, Korean Patent Application No. 1998-073605 discloses a method for preparing a catalyst suspension by controlling weight of water based on total weight of metal salts, and Korean Patent Application No. 1998-073604 discloses that catalyst performance differs according to particle size.

As can be seen from the prior patent, studies on a method for preparing a catalyst that can show a higher acrolein conversion rate and acrylic acid yield have actively progressed, and are continuously required.

SUMMARY OF THE INVENTION

It is an object of the present invention to provide a method for preparing a catalyst for partial oxidation of acrolein that has a superior acrolein conversion rate, and that can improve acrylic acid activity, selectivity, and yield.

It is another object of the present invention to provide a catalyst for partial oxidation of acrolein that has superior acrylic acid activity and selectivity.

In order to achieve these objects, the present invention provides a method for preparing a catalyst for partial oxidation of acrolein represented by the following Chemical Formula 1, comprising the steps of:

a) dissolving one or more kinds of metal salts selected from the group consisting of molybdenum, tungsten, iron, copper, strontium, bismuth, chrome, tin, antimony, potassium, an alkali earth metal, and a mixture thereof in water to prepare a catalyst suspension;

b) introducing a base solution and an acid solution into the a) catalyst suspension to control acidity of the catalyst suspension to 3.5 to 6.5;

c) contacting the b) catalyst suspension of which acidity is controlled with an inert support to support the catalyst thereon; and d) drying and firing the c) supported catalyst.

 [Chemical Formula 1]

wherein

Mo is molybdenum, W is tungsten, V is vanadium;

A is iron, copper, bismuth, chrome, tin, antimony or potassium;

B is an alkali earth metal; and a, b, c, d, and e respectively represent the atomic ratio of each metal, and when a is 12, b is 1~5, c is 1~6, d is 1~5, and e is 0~3, and x is determined according to the oxidation state of each metal.

In addition, the present invention provides a catalyst for partial oxidation of acrolein, which is prepared by introducing a base solution and an acid solution into a catalyst suspension prepared by dissolving one or more kinds of metal salts selected from the group consisting of molybdenum, tungsten, copper, iron, strontium, bismuth, chrome, tin, antimony, potassium, and an alkali earth metal in water to control acidity of the catalyst suspension to 3.5 to 6.5, contacting the catalyst suspension of which acidity is controlled with an inert support to support the catalyst thereon, and drying and firing the supported catalyst.

DETAILED DESCRIPTION OF THE PREFERRED EMBODIMENTS

The present invention will now be explained in more detail.

The present inventors, during studies on a catalyst capable of showing a higher acrolein conversion rate and acrylic acid yield, prepared a catalyst by introducing a base solution and an acid solution into a catalyst suspension prepared by dissolving metal salts in water to control acidity of the catalyst suspension to 3.5 to 6.5, contacting the acidity-controlled catalyst suspension with an inert support to support the catalyst thereon, and drying and firing the supported catalyst, and as a result, identified that acrolein conversion rate, acrylic acid activity, selectivity, and yield can be remarkably improved, and completed the present invention.

The method of the present invention for preparing a catalyst that is used for partially oxidizing acrolein to acrylic acid is as follows.

a) Preparation of a Catalyst Suspension

This step is to dissolve salts of metal ingredients of a catalyst for partially oxidizing acrolein to acrylic acid in water to prepare a catalyst suspension.

As the metal ingredients, molybdenum, tungsten, iron, copper, strontium, bismuth, chrome, tin, antimony, potassium, or an alkali earth metal, etc. can be used.

The metal ingredients are preferably dissolved in water in a concentration of 0.2 M based on the metal salts.

If the metal salts are dissolved and agitated in water, cationic metal salts and anionic metal salts existing in the water react with each other below a specific temperature to form a precipitate, and when agitation is stopped, the precipitate rapidly settles to obtain a suspension in which phase separation from the water layer occurs.

In the above prepared catalyst suspension, particle size of the metal salts largely influences catalyst performance, and the particle size of the metal salts is preferably up to 10 μm.

b) Acidity Control

This step is to introduce a base solution and an acid solution into the above prepared catalyst suspension to control the acidity thereof to 3.5 to 6.5.

As the base solution, one having an amine group such as ammonia, pyridine, methyl amine, or ethyl diamine, etc., or an organic base solution having 1~10 carbon atoms can be used.

As the acid solution, an organic acid solution having 1-10 carbon atoms such as acetic acid, citric acid, etc. can be used.

The acidity of the catalyst suspension, which is controlled by introducing the above base solution and acid solution, is preferably 3.5 to 6.5, and more preferably 4.0 to 5.5. If the acidity is less than 3.5 or more than 6.5, catalyst reactivity deteriorates.

When the acidity of the catalyst suspension is controlled by introducing the base solution and acid solution, a suspension with a smaller particle size can be prepared, compared to a catalyst suspension of which acidity is not controlled using a base solution and an acid solution. A catalyst prepared using the above prepared catalyst suspension has superior activity and selectivity. BET surface area of the prepared catalyst is preferably 4~15.

c) Support

This step is to contact the catalyst suspension of which acidity is controlled with an inert support to support the catalyst thereon.

The inert support and support conditions are not specifically limited, and the suspension can be supported on a common inert support such as alumina, silica, etc. by a common support method such as vacuum or nozzle spraying, etc. In the present invention, support is conducted using a fixed bed multi-tube reactor under commonly known reaction conditions.

d) Drying and Firing

This step is to dry and fire the supported catalyst.

The firing is preferably conducted at a temperature of 350 to 450 □ for 4 to 6 hours, and more preferably at 400 □ for 5 hours. The firing is preferably conducted under an air atmosphere.

The present invention provides a catalyst for partial oxidation of acrolein prepared by the above method.

If the above prepared catalyst is used for partial oxidation of acrolein to acrylic acid, the acrolein conversion rate can be improved, and acrylic acid activity, selectivity, and yield can be remarkably improved.

The present invention will now be explained with reference to the following examples. However, these are only to illustrate the present invention and the present invention is not limited to them.

EXAMPLES

Example 1

To a 500 cc glass reactor, 400 mL of distilled water was added while stirring and heating to 100 □. 100 g of ammonium molybdate, 18.48 g of ammonium paratungstate, 16.56 g of ammonium methavanadate, 22.81 g of copper nitrate, and 4.99 g of strontium nitrate were sequentially introduced into the reactor, and then completely dissolved to prepare a catalyst suspension. The temperature of the catalyst suspension was lowered to room temperature or another desired temperature, and then ammonia water and nitrate were introduced to control the acidity of the catalyst suspension to 3.8.

The catalyst suspension of which acidity was controlled was applied to an inert support using a spray nozzle, and dried by hot air at 90 □ to thereby coat the support. The obtained supported catalyst was dried at 120□, and fired at 400 □ for 5 hours with air circulation to prepare a catalyst. After the firing, the amount of the coated supported catalyst was 25 wt % of the total amount, and the compositional ratio of the catalyst elements excluding oxygen was $Mo_{12}W_{1.5}V_3Cu_2Sr_{0.3}$.

Example 2

A catalyst was prepared by the same method as in Example 1, except that the acidity of the catalyst suspension was controlled to 4.5 by introducing ammonia water and acetic acid.

Example 3

A catalyst was prepared by the same method as in Example 1, except that the acidity of the catalyst suspension was controlled to 6.0 by introducing ammonia water and citric acid.

Example 4

A catalyst was prepared by the same method as in Example 1, except that the acidity of the catalyst suspension was controlled to 4.5 by introducing a pyridine solution and nitric acid.

Example 5

A catalyst was prepared by the same method as in Example 1, except that the acidity of the catalyst suspension was controlled to 4.5 by introducing a methylamine solution and acetic acid.

Example 6

A catalyst was prepared by the same method as in Example 1, except that the acidity of the catalyst suspension was controlled to 4.5 by introducing an ethylene diamine solution and citric acid.

Comparative Example 1

To a 500 cc glass reactor, 400 mL of distilled water was added while stirring and heating to 100 □. 100 g of ammonium molybdate, 18.48 g of ammonium paratungstate, 16.56 g of ammonium methavanadate, 22.81 g of copper nitrate, and 4.99 g of strontium nitrate were sequentially introduced into the reactor, and completely dissolved to prepare a catalyst suspension of pH 4.5~5.0.

The catalyst suspension was applied to an inert support using a spray nozzle, and dried by hot air at 90 □ to thereby coat the support. The obtained supported catalyst was dried at 120 □, and then fired at 400 □ for 5 hours with air circulation to prepare a catalyst. After the firing, the amount of the coated supported catalyst was 25 wt % of the total amount, and the compositional ratio of catalyst elements excluding oxygen was $Mo_{12}W_{1.5}V_3Cu_2Sr_{0.5}$.

Experiment 1: Catalyst Activity Test

The catalysts prepared in Examples 1 to 6 and Comparative Example 1 were individually charged into a reactor with a temperature of 250~300 □ and a pressure of 1~3 atm. Then, a gas mixture comprising acrolein, oxygen, vapor, and nitrogen in a volume ratio of 7.0:5.6:15:72.4 was introduced onto each catalyst at a space velocity of 500~2000 hours (STP) to conduct partial oxidation of acrolein. The acrolein conversion rate, acrylic acid selectivity, and acrylic acid yield were calculated according to the following Equations 1 to 3, and the results are shown in the following Table 1.

Acrolein conversion rate (%)=moles of reacted acrolein/moles of supplied acrolein×100     [Equation 1]

Acrylic acid selectivity (%)=moles of produced acrylic acid/moles of reacted acrolein×100     [Equation 2]

Yield (%)=moles of produced acrylic acid/moles of supplied acrolein×100     [Equation 3]

TABLE 1

| | Example | | | | | | Comparative |
|---|---|---|---|---|---|---|---|
| | 1 | 2 | 3 | 4 | 5 | 6 | Example 1 |
| Base solution | ammonia | ammonia | ammonia | Pyridine | methylamine | Ethyldiamine | — |
| Acid solution | Nitric acid | Acetic acid | Citric acid | Nitric acid | Acetic acid | Citric acid | — |
| Catalyst component | $Mo_{12}W_{1.5}V_3Cu_2$ $Sr_{0.3}$ | $Mo_{12}W_{1.5}V_3Cu_2$ $Sr_{0.3}$ | $Mo_{12}W_{1.5}V_3Cu_2$ $Sr_{0.3}$ | $Mo_{12}W_{1.5}V_3Cu_2$ $Sr_{0.3}$ | $Mo_{12}W_{1.5}V_3Cu_2$ $Sr_{0.3}$ | $Mo_{12}W_{1.5}V_3Cu_2$ $Sr_{0.3}$ | $Mo_{12}W_{1.5}V_3Cu_2$ $Sr_{0.5}$ |
| Reaction temperature | 280° C. | 280° C. | 280° C. | 280° C. | 280° C. | 280° C. | 280° C. |
| Acrolein conversion rate (%) | 99.42 | 99.15 | 99.07 | 98.45 | 99.07 | 97.15 | 96.21 |
| Acrylic acid selectivity (%) | 89.56 | 91.62 | 91.91 | 89.84 | 89.98 | 93.82 | 87.54 |
| Acrylic acid yield (%) | 89.05 | 90.85 | 91.12 | 88.45 | 89.15 | 91.15 | 84.23 |

As can be seen from the above Table 1, Examples 1 to 4 of the present invention, in which acrolein partial oxidation was conducted using catalysts which were prepared by controlling acidities of the catalyst suspension with an acid solution and a base solution, showed superior acrolein conversion rates, acrylic acid selectivity, and acrylic acid yields compared to Comparative Example 1.

According to the present invention, when preparing acrylic acid by partial oxidation of acrolein, the acrolein conversion rate can be improved, and acrylic acid activity, selectivity, and yield can be remarkably improved.

What is claimed is:

1. A method for preparing a catalyst for partial oxidation of acrolein, represented by the following Chemical Formula 1 and having a BET surface area of 4 to 15 m²/g, comprising the steps of:
   a) dissolving the following metal salts:
      i) a molybdenum salt,
      ii) a tungsten salt,
      iii) a vanadium salt,
      iv) a salt of a metal selected from the group consisting of iron, copper, bismuth, chromium, tin, antimony, and potassium, and
      v) a salt of an alkaline earth metal in water to prepare a catalyst suspension;
   b) introducing a base solution and an acid solution into the a) catalyst suspension to control acidity of the catalyst suspension to a pH of 3.5 to 6.5, wherein the acid solution is an organic acid solution having 1 to 10 carbon atoms;
   c) contacting the b) catalyst suspension of which acidity is controlled with an inert support to support the catalyst thereon; and
   d) drying and firing the c) supported catalyst:

$$MO_aW_bV_cA_dB_eO_x$$     [Chemical Formula 1]

wherein

Mo is molybdenum, W is tungsten, V is vanadium;

A is iron, copper, bismuth, chromium, tin, antimony, or potassium;

B is an alkaline earth metal; and a, b, c, d, and e respectively represent the atomic ratio of each metal, and when a is 12, b is 1-5, c is 1-6, d is 1-5, and e is $0 < e \leq 3$, and x is determined according to the oxidation state of each metal.

2. The method for preparing a catalyst for partial oxidation of acrolein according to claim 1, wherein in the a) catalyst suspension, the maximum particle size of the metal salts is 10 μm.

3. The method for preparing a catalyst for partial oxidation of acrolein according to claim 2, wherein the b) base solution is a base solution of one or more selected from the group consisting of ammonia, pyridine, methylamine, and ethyldiamine, or an organic base solution having 1-10 carbon atoms.

4. The method for preparing a catalyst for partial oxidation of acrolein according to claim 2, wherein the b) acid solution is one or more members selected from the group consisting of acetic acid and citric acid.

5. The method for preparing a catalyst for partial oxidation of acrolein according to claim 1, wherein in step b), the acidity of the catalyst suspension is controlled to a pH of 4.0 to 5.5.

6. The method for preparing a catalyst for partial oxidation of acrolein according to claim 1, wherein e is 0.5-3.

7. A catalyst for partial oxidation of acrolein represented by the following Chemical Formula 1, which has a BET surface area of 4 to 15 m²/g, prepared by introducing an acid solution and a base solution into a catalyst suspension prepared by dissolving the following metal salts i) a molybdenum salt, ii) a tungsten salt, iii) a vanadium salt, iv) a salt of a metal selected from the group consisting of iron, copper, bismuth, chromium, tin, antimony, and potassium, and v) a salt of an alkaline earth metal to control the acidity of the catalyst suspension to a pH of 3.5 to 6.5, the acid solution being an organic acid solution having 1 to 10 carbon atoms, contacting the catalyst suspension of which acidity is controlled with an inert support to support the catalyst thereon, and then drying and firing the supported catalyst:

$$Mo_a W_b V_c A_d B_e O_x \quad \text{[Chemical Formula 1]}$$

wherein

Mo is molybdenum, W is tungsten, V is vanadium;

A is iron, copper, bismuth, chromium, tin, antimony, or potassium;

B is an alkaline earth metal; and a, b, c, d, and e respectively represent the atomic ratio of each metal, and when a is 12, b is 1-5, c is 1-6, d is 1-5, and e is 0<e≦3, and x is determined according to the oxidation state of each metal.

8. The catalyst for partial oxidation of acrolein according to claim 7, wherein the acidity of the catalyst suspension is controlled to a pH of 4.0 to 5.5.

9. The catalyst for partial oxidation of acrolein according to claim 5, wherein e is 0.5-3.

* * * * *